United States Patent [19]

Smale

[11] 4,443,599

[45] Apr. 17, 1984

[54] 8-OXO-3-OXA-1-AZABICYCLO[4.2.0]OCTANES CONTAINING A CHIRAL CENTER

[75] Inventor: Terence C. Smale, Epsom Downs, England

[73] Assignee: Beecham Group p.l.c., England

[21] Appl. No.: 377,697

[22] Filed: May 12, 1982

[30] Foreign Application Priority Data

May 14, 1981 [GB] United Kingdom ............... 8114848

[51] Int. Cl.$^3$ ............................................. C07D 498/04
[52] U.S. Cl. ................................... 544/90; 424/248.57
[58] Field of Search ........................ 544/90; 424/248.57

[56] References Cited

U.S. PATENT DOCUMENTS

| | | | |
|---|---|---|---|
| 4,122,262 | 10/1978 | Buckley et al. ...................... | 544/90 |
| 4,245,089 | 1/1981 | Ponsford et al. ................... | 544/90 X |
| 4,323,567 | 4/1982 | Narisada et al. ................... | 544/90 X |
| 4,348,320 | 9/1982 | Bouffard et al. ................... | 544/90 X |

FOREIGN PATENT DOCUMENTS 18594  11/1980  European Pat. Off. .
2013667  8/1979  United Kingdom .

OTHER PUBLICATIONS

Bouffard et al., Journal of Organic Chemistry, vol. 45, No. 6 (1980), pp. 927–1176.
Ponsford et al., Journal of the Chemical Society, No. 19 (1979), pp. 846–847.
Ponsford et al., Journal of the Chemical Society, No. 21 (1980), pp. 1085–1086.

Primary Examiner—Richard Raymond
Attorney, Agent, or Firm—Jacobs & Jacobs

[57] ABSTRACT

There is provided a process for the preparation of an enantiomer of a compound of formula (I) which process comprises separation thereof from a mixture of diastereoisomers of a compound of the formula (I):

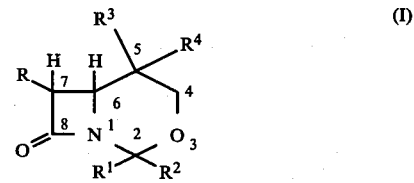

wherein R is acetyl, α-hydroxyethyl or a protected derivative thereof, and $R^1$ and $R^2$ are substituted or unsubstituted hydrocarbon groups, or are joined so as to form a carbocyclic or heterocyclic ring; at least one of $R^1$ and $R^2$ containing a chiral center, such that the enantiomer can be separated thereby; and $R^3$ and $R^4$ are independently hydrogen or an organic group bonded via a carbon atom to the tetrahydro-oxazine ring, or $R^3$ and $R^4$ are joined so as to form together with the carbon atom to which they are attached an optionally substituted $C_{3-7}$ cycloalkyl or optionally substituted heterocyclyl ring.

The enantiomer is of use in the preparation of optically active carbapenem antibiotics.

3 Claims, No Drawings

8-OXO-3-OXA-1-AZABICYCLO[4.2.0]OCTANES CONTAINING A CHIRAL CENTER

The present invention relates to a chemical process and to intermediates used therein.

U.K. Patent Specification No. 2013667A discloses compounds of the formula (O) wherein the configuration about the β-lactam ring is trans:

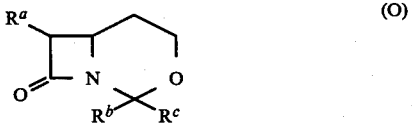

and wherein $R^a$ is acetyl or 1-hydroxyethyl, and $R^b$ and $R^c$ are independently alkyl of up to 3 carbon atoms, or $R^b$ and $R^c$ together with the carbon atom to which they are attached form a spirocyclopentyl or spirocyclohexyl ring.

The present invention provides a process for the preparation of an enantiomer of a compound of formula (I) which process comprises separation thereof from a mixture of diastereoisomers of a compound of the formula (I):

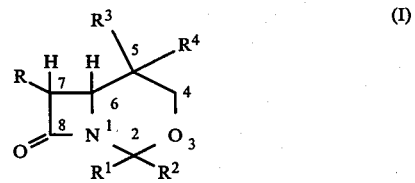

wherein R is acetyl, α-hydroxyethyl or a protected derivative thereof, and $R^1$ and $R^2$ are substituted or unsubstituted hydrocarbon groups, or are joined so as to form a carbocyclic or heterocyclic ring; at least one of $R^1$ and $R^2$ containing a chiral centre, such that the enantiomer can be separated thereby; and $R^3$ and $R^4$ are independently hydrogen or an organic group bonded via a carbon atom to the tetrahydro-oxazine ring, or $R^3$ and $R^4$ are joined so as to form together with the carbon atom to which they are attached an optionally substituted $C_{3-7}$ cycloalkyl or optionally substituted heterocyclyl ring.

By chiral centre we mean a centre of optical activity, and all molecules of the compound of the formula (I) have a defined absolute configuration at this centre i.e. this centre has been resolved at an earlier stage of the synthesis or, preferably, the moiety bearing the chiral centre has been introduced into the synthesis in resolved form, for example when $R^1$ and $R^2$ together represent spiro (R)-3-methylcyclohexane this moiety is derived from the naturally occurring (+)-pulegone.

The process of this invention may be performed on a compound of the formula (I) wherein R is acetyl or a protected derivative thereof. Preferably R is acetyl.

In an alternative aspect the process of this invention is performed on a compound of the formula (I) wherein R is α-hydroxyethyl or a protected derivative thereof, for example the α-hydroxy group may be protected in conventional manner such as by acylation. Suitable acyl groups include carboxylic acyl, sulphonyl and phosphoryl. Particularly suitable acyl groups include those of the sub-formula $COR^5$ and $COOR^5$ wherein $R^5$ is $C_{1-6}$ alkyl such as methyl or ethyl, or aryl $C_{1-6}$ alkyl wherein aryl includes phenyl optionally substituted by one, two or three groups selected from $C_{1-6}$ alkyl, $C_{1-6}$ alkoxy, nitro and halo, such as benzyl and optionally substituted benzyl. Further particularly suitable acyl protecting groups include —$SO_3H$ and salts and $C_{1-6}$ alkyl esters thereof.

Suitably $R^1$ and $R^2$ are different unsubstituted or substituted hydrocarbon groups of up to 20 carbon atoms. Preferably $R^1$ is selected from $C_{1-6}$ alkyl such as methyl, ethyl, propyl and butyl. Preferably $R^2$ is selected from a $C_{3-10}$ hydrocarbon group, for example $C_{3-10}$ alkyl such as sec-butyl, and $C_{8-10}$ arylalkyl such as $C_6H_5CH(CH_3)$—.

Suitably $R^1$ and $R^2$ are joined so as to form together with the carbon atom to which they are joined a substituted carbocyclic or heterocyclic ring, where for example the carbocyclic or heterocyclic ring contains from 3 to 8 ring atoms. Suitably in a heterocyclic ring one, two or three heteroatoms are present selected from oxygen, nitrogen and sulphur.

Suitable substituents for $R^1$ and $R^2$, either when independent or joined so as to form a ring, include hydroxy, bromine, chlorine, fluorine, carboxylic acid or salt or ester thereof, azido, tetrazolyl, alkanoyl, alkanoyloxy, aroyloxy, aroyl, aralkanoyloxy, aroxy, amino, protected amino, nitro, $C_{1-6}$ alkoxy, $C_{1-6}$ alkyl, aryl, $C_{1-6}$ alkylthio and arylthio.

Suitably $R^1$ and $R^2$ together with the carbon atom to which they are joined form an asymmetrically substituted cyclopentane or cyclohexane ring. Suitable substituents include $C_{1-6}$ alkyl, for example methyl, ethyl and propyl. Preferably $R^1$ and $R^2$ together with the carbon atom to which they are joined form a methylcyclohexane ring or ethylcyclohexane ring, for example a (R)-3-methylcyclohexane ring. As is evident from the foregoing the exact nature of the substitution is unimportant, provided that a chiral centre is present in either $R^1$ and/or $R^2$; for example the substituted cyclopentane or cyclohexane ring referred to above may be part of a steroid or terpene.

In one aspect $R^3$ is a hydrogen atom. In a further aspect $R^4$ is a hydrogen atom.

Suitably $R^3$ and $R^4$ represent hydrocarbon groups, in particular having from 1 to 20 carbon atoms, especially 1 to 10 carbon atoms.

For example the groups $R^3$ and $R^4$ may be selected from $C_{1-6}$ alkyl, $C_{3-7}$ cycloalkyl, $C_{3-7}$ cycloalkyl ($C_{1-6}$) alkyl, aryl ($C_{1-6}$)alkyl, heteroaryl ($C_{1-6}$)alkyl, heterocyclyl ($C_{1-6}$)alkyl, heterocyclyl, aryl and heteroaryl. Suitably the hetero atom or heteroatoms in the above named heteroaryl and/or heterocyclyl moieties are selected from 1 to 4 oxygen, nitrogen or sulphur atoms.

Suitably also $R^3$ and $R^4$ are joined so as to form together with the carbon atom to which they are attached an optionally substituted $C_{3-7}$ cycloalkyl or optionally substituted heterocyclyl ring; for example cyclopropyl, cyclobutyl, cyclopentyl or cyclohexyl. Of these cyclopropyl is preferred.

More suitably groups $R^3$ and $R^4$ may be selected from $C_{1-6}$ alkyl such as methyl, ethyl or n-propyl; aryl ($C_{1-6}$) alkyl such as benzyl or phenethyl; or $C_{3-7}$ cycloalkyl such as cyclohexyl.

Preferably $R^3$ is $C_{1-6}$ alkyl, in particular methyl and $R^4$ is $C_{1-6}$ alkyl, in particular methyl.

In a further preferred aspect $R^3$ and $R^4$ are independently hydrogen atoms.

The compound of the formula (I) wherein R is acetyl, either as an enantiomer or as a mixture of diastereoisomers may be reduced in conventional manner for example hydride reduction. A suitable method of reduction employs sodium borohydride at a slightly depressed temperature, for example at about 0° C. in an alcoholic solvent such as ethanol. A preferred method utilises potassium selectride, i.e. potassium tri- sec-butylborohydride, as this yields the compound of the formula (I) wherein R is α-hydroxyethyl in predominantly the 9R absolute stereochemistry.

The separation of the enantiomer of the compound of the formula (I) from a mixture of diastereoisomers of the formula (I) may be performed by crystallization and/or chromatography. Suitably chromatography may be performed on columns of silica gel eluting with halohydrocarbons such as chloroform. Crystallisation of enantiomer may be effected by crystallisation from an organic solvent or a mixture of organic solvents, for example a hydrocarbon such as hexane.

The compounds of the formula (I) are novel and as such form part of this invention.

In another aspect the present invention provides a process for the preparation of a compound of the formula (I) which process comprises the ring-closing cyclisation of a compound of the formula (II):

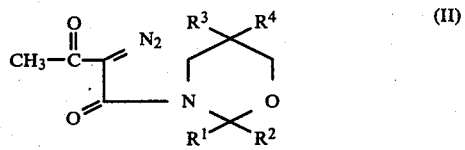

or protected derivative thereof, wherein $R^1$–$R^4$ are as hereinbefore defined; and if it is desired to form a compound of the formula (I) wherein R is α-hydroxyethyl or a protected derivative thereof, subsequently
(i) removing a protecting group if present,
(ii) reducing the acetyl group,
(iii) optionally protecting the resultant α-hydroxyethyl group.

In one aspect the ring-closing cyclisation may be effected by photolysis, for example by irradiation. This may be conveniently performed utilising a 450 W Hanovia medium pressure mercury lamp with a pyrex reaction vessel. Generally the photolysis reaction is carried out at a depressed temperature, for example −20° C. to −80° C., in an inert solvent such as diethyl ether.

In another aspect the cyclization may be effected by metal-catalysed carbenoid insertion such as by a rhodium (II) species, for example rhodium (II) acetate, in an organic solvent such as benzene or toluene, preferably benzene.

The compounds of the formula (II) may be prepared by the reaction of a compound of the formula (III):

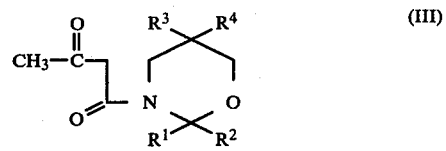

wherein $R^1$–$R^4$ are as hereinbefore defined, with a diazo-transfer reagent such as methanesulphonyl azide in the presence of a tertiary base such as triethylamine. Generally the reaction is performed in an organic solvent such as benzene at an approximately ambient temperature.

The compounds of the formula (III) may be prepared by the reaction of diketene with a compound of the formula (IV):

wherein $R^1$–$R^4$ are as hereinbefore defined.

The compounds of the formula (IV) may be prepared by the methods of U.S. Pat. No. 4,245,089 and Hancock et al *J. Amer. Chem. Soc.* 1944, 66, 1947.

The compounds of the formula (I) also may be prepared by the methods of European Patent Application Publication No. 0018954.

The enantiomers of the formula (I) preferably those with the stereochemistry depicted in formula (V):

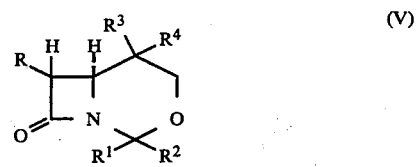

may be converted to antibacterial agents in conventional manner, for example see the disclosures of West German OLS No. 2751597 and the aforementioned U.S. Patent. The use of an enantiomer is particularly advantageous in that it enables optically active β-lactam antibacterial agents, for example carbapenems, to be prepared.

Thus in another aspect the present invention provides the use of a enantiomer of a compound of the formula (I) in the preparation of a β-lactam antibacterial agent.

The following Examples illustrate the invention:

EXAMPLE 1

3-Acetoacetyltetrahydro-1,3-oxazine-2-spiro-1'-[(3'R)-3'-methylcyclohexane]

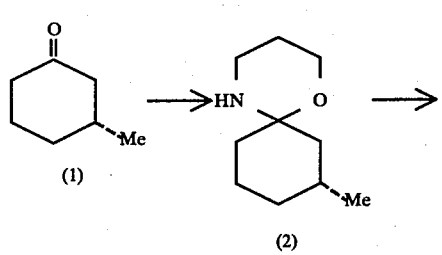

-continued

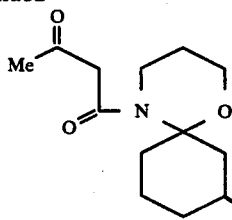

(3)

A solution of (R)-(+)-3-methylcyclohexanone (1) (20.0 g) and 3-amino-1-propanol (13.4 g) in benzene (300 ml) was heated at reflux for 24 h in an apparatus with provision for azeotropic water removal. The resulting solution, which contained the tetrahydro-1,3-oxazine (2), was cooled in an ice bath and treated with freshly distilled diketene (13.8 ml). The reaction mixture was stirred at 0° C. for 3 h and then concentrated. Chromatography of the residue on silica gel 60 (<230 mesh ASTM) eluting with ethyl acetate/60°-80° petroleum ether 1:1 gave 3-acetoacetyl-1,3-oxazine-2-spiro-1'-[(3'R)-3'-methylcyclohexane] (3) (30.5 g) as a colourless viscous liquid, $\nu_{max}$. (CHCl$_3$) 3 430 br, 1 720, and 1 635 cm$^{-1}$; δ (CDCl$_3$) 0.90 (3H, d, J 7 Hz, CH$_3$), 1.5–2.7 (11H, m, cyclohexyl and 5-H$_2$), 2.27 (3H, s, COCH$_3$), 3.42 (2H, dd, J 7 and 6 Hz, 4-H$_2$), 3.51 (2H, s, COCH$_2$CO), and 3.80 (2H, t, J 8 Hz, 6-H$_2$).

EXAMPLE 2

3-Acetodiazoacetyltetrahydro-1,3-oxazine-2-spiro-1'-[(3'R)-3'-methylcyclohexane]

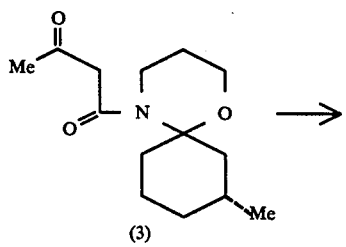

(3)

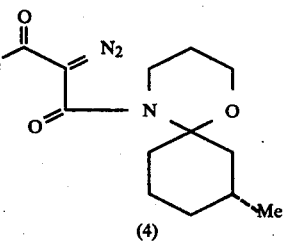

(4)

A stirred solution of the tetrahydro-1,3-oxazine (3) (30.5 g) in dry benzene (200 ml) was cooled in an ice bath and treated with triethylamine (25.1 ml) followed by methanesulphonyl azide (21.8 g) in benzene (100 ml). After a period of 2 h the cooling was removed and the reaction stirred at room temperature overnight. It was then concentrated and chromatographed on silica gel 60 (<230 mesh ASTM) eluting with ethyl acetate/hexane 3:7 grading to 7:3 to provide 3-acetodiazoacetyltetrahydro-1,3-oxazine-2-spiro-1'-[(3'R)-3'-methylcyclohexane] (4) as a yellow gum (33.2 g), $\nu_{max}$. (CHCl$_3$) 2 140, 2 110, and 1 640 cm$^{-1}$; δ (CDCl$_3$) 0.91 (3H, d, J 7 Hz, CH$_3$), 1.5–2.6 (11H, m, cyclohexyl and 5-H$_2$), 2.34 (3H, s, COCH$_3$), 3.47 (2H, dd, J 8 and 6 Hz, 4-H$_2$), and 3.83 (2H, t, J 7 Hz, 6-H$_2$).

EXAMPLE 3

(6R, 7S)-7-Acetyl-8-oxo-3-oxa-1-azabicyclo[4.2.0]octane-2-spiro-1'-[(3'R)-3'-methylcyclohexane]

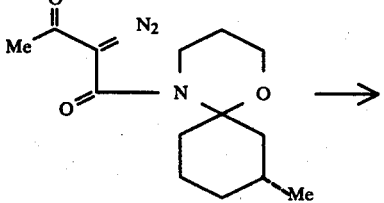
(4)

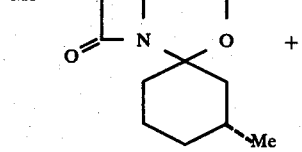
(5)

+

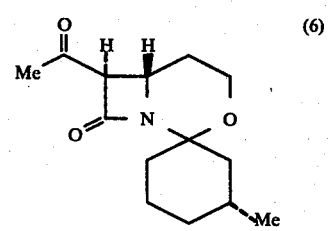
(6)

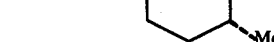

A stirred suspension of rhodium (II) acetate dimer (0.075 g) in dry benzene (3 ml) was treated with a solution of the diazo compound (4) (0.65 g) in dry benzene (2 ml) over a period of a few minutes. The mixture was stirred at room temperature until all the diazo compound had been consumed (20 h) and the catalyst was then filtered off and the filtrate concentrated. This gum was then chromatographed on silica gel 60 (<230 mesh ASTM) eluting with ethyl acetate/hexane 3:7 to give a mixture (0.38 g) of the (6R) (5) and (6S) (6) diastereoisomers of the tricyclic system. This mixture was carefully rechromatographed on silica gel 60 (<230 mesh ASTM) eluting with chloroform and the eluted fractions were split into two batches and then bulked and concentrated. This gave faster moving material (0.18 g) and slower running material (0.15 g), both as colourless gums. On standing in the refrigerator the slow running fraction crystallised and was recrystallised from hexane to give pure (6R, 7S)-7-acetyl-8-oxo-3-oxa-1-azabicyclo[4.2.0]-octane-2-spiro-1'-[(3'R)-3'-methylcyclohexane] (5) (0.08 g); m.p. 82°–84° C.; $[\alpha]_D^{20}$+25° (c 1 in CHCl$_3$); $\nu_{max}$. (CHCl$_3$) 1 740 and 1 710 cm$^{-1}$; δ (CDCl$_3$) 0.89 (3H, d, J 7 Hz, CH$_3$), 1.5–1.8 (8H, m, cyclohexyl and 5-H), 1.93 (1H, ddt, J 14,5, and 3 Hz, 5-H), 2.0–2.3 (3H, m, cyclohexyl), 2.31 (3H, s, COCH$_3$), 3.76 (1H, ddd, J 13,5, and 3 Hz, 4-H), 3.83 (1H, d, J 2 Hz, 7-H), 3.87 (1H, ddd, J 13, 6, and 3 Hz, 4-H), and 4.02 (1H, ddd, J 11, 5 and 2 Hz, 6-H) (Found: C, 66.6; H, 8.4; N, 5.4%. C$_{14}$H$_{21}$NO$_3$ requires C, 66.9; H, 8.4, N, 5.6%).

EXAMPLE 4

(6R, 7S)-7-[(1R)-1-hydroxyethyl]-8-oxo-3-oxa-1-azabicyclo[4.2.0]octane-2-spiro-1'-[(3'R)-3'-methylcyclohexane]

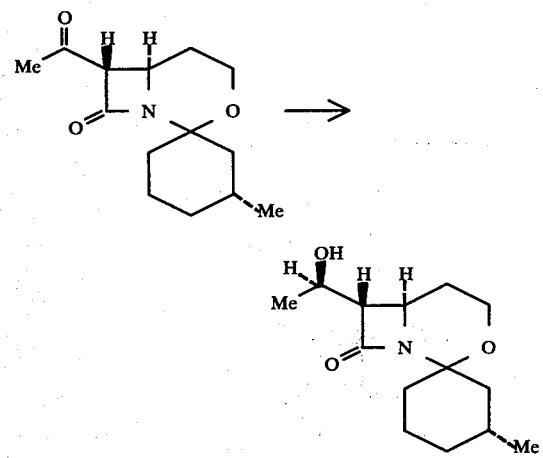

The ketone (5) (1.98 g) was dissolved in dry tetrahydrofuran (100 ml) and stirred at 0° C. under argon. It was treated with a 0.5 M tetrahydrofuran solution of potassium tri-sec-butyl borohydride (19.0 ml) and the cooling bath removed. After a period of 45 min, the reaction mixture was hydrolysed by addition of water (5 ml) and the organic solvent then removed under reduced pressure. The residue was dissolved in ethyl acetate, washed with brine, dried over sodium sulphate, and concentrated. The residue was chromatographed on silica gel 60 (<230 mesh ASTM) eluting with ethyl acetate/hexane 1:1 grading to 4:1 to give (6R, 7S)-7-[(1R)-1-hydroxyethyl]-8-oxo-3-oxa-1-azabicyclo-[4.2.0]octane-2-spiro-1'-[(3'R)-3'-methylcyclohexane](7) as a colourless gum (1.70 g), $v_{max}$. (CHCl$_3$) 3 410 and 1 725 cm$^{-1}$; δ (CDCl$_3$) 0.90 (3 H, d, J 7 Hz, CH$_3$), 0.9–1.1 (2 H, m, cyclohexyl), 1.30 (3 H, d, J 7 Hz, CH$_3$C—O—), 1.5–1.8 (6 H, m, cyclohexyl, OH and 5-H), 1.91 (1 H, ddt, J 13, 5 and 3 Hz, 5-H), 2.1–2.4 (3 H, m, cyclohexyl), 2.82 (1H, dd, J 6 and 2 Hz, 7-H), 3.61 (1 H, ddd, J 11, 5 and 2 Hz, 6-H), 3.77 (1 H, td, J 12 and 3 Hz, 4-H), 3.86 (1 H, ddd, J 12, 6, and 3 Hz, 4-H), and 4.13 (1 H, br m, CH—O) (Found: M$^+$, 253.169 0. C$_{14}$H$_{23}$NO$_3$ requires M, 253.167 6).

The product contained a small amount of the (S)-epimer of the hydroxyethyl side chain.

EXAMPLE 5

(6R, 7S)-7-[(1R)-1-p-nitrobenzyloxycarbonyloxyethyl]-8-oxo-3-oxa-1-azabicyclo[4.2.0]octane-2-spiro-1'-[(3'R)-3'-methylcyclohexane]

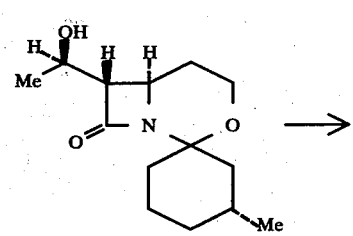

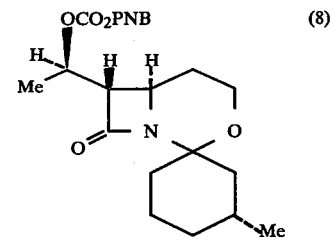

A solution of hydroxy compound (7) (1.70 g) in dry tetrahydrofuran (100 ml) was stirred under argon at −70° C. and treated with a 1.55 M hexane solution of n-butyl lithium (5.2 ml). After a period of 10 mins, a solution of p-nitrobenzyl chloroformate (2.18 g) in dry tetrahydrofuran (10 ml) was added, and the cooling bath removed. The reaction was maintained at room temperature for 45 mins and water (5ml) then added. The solution was concentrated, dissolved in ethyl acetate, washed with brine, dried over sodium sulphate and reconcentrated. Chromatography on silica gel 60 (<230 mesh ASTM) eluting with ethyl acetate/hexane 3:7 grading to 7:3 gave (6R, 7S)-7-[(1R)-1-p-nitrobenzyloxycarbonyloxyethyl]-8-oxo-3-oxa-1-azabicyclo[4.2.0]octane-2-spiro-1'-[(3'R)-3'-methylcyclohexane] (8) as a colourless gum (2.32 g), $v_{max}$. (CHCl$_3$) 1 740, 1 605, and 1 520 cm$^{-1}$; δ(CDCl$_3$) 0.89 (3 H, d, J 6 Hz, CH$_3$), 0.9–1.0 (2 H, m, cyclohexyl), 1.45 (3 H, d, J 6 Hz, CH$_3$—C—), 1.5–2.3 (9 H, m, cyclohexyl and 5-H$_2$), 2.95 (1 H, dd, J 8 and 2 Hz, 7-H), 3.55 (1 H, ddd, J 11, 5, and 2 Hz, 6-H), 3.74 (1 H, td, J 12 and 2 Hz, 4-H), 3.84 (1 H, ddd, J 12, 5, and 2 Hz, 4-H), 5.04 (1 H, dq, J 8 and 6 Hz, CH-O), 5.25 (2 H, s, benzyl CH$_2$), 7.55 and 8.25 (4 H, 2d, J 9 Hz, nitrobenzyl) (Found: M$^+$, 432.185 7. C$_{22}$H$_{28}$N$_2$O$_7$ requires M, 432.189 5).

EXAMPLE 6

(3S, 4R)-4-(2-Hydroxyethyl)-3-[(1R)-1-p-nitrobenzyloxycarbonyloxyethyl]-azetidin-2-one

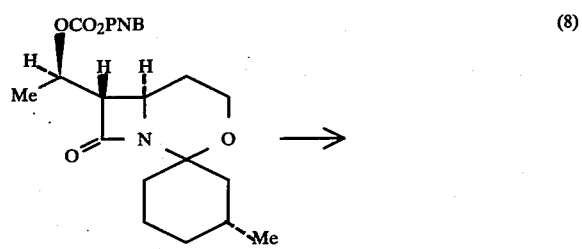

A solution of the tricyclic compound (8) (2.30 g) in acetone (120 ml) was stirred at room temperature and treated with a solution of concentrated sulphuric acid (s.g. 1.84) (3 ml) in water (12 ml). After a period of 2.5 h the reaction was neutralised by addition of saturated aqueous sodium bicarbonate (ca 90 ml), and the acetone then removed under reduced pressure. The aqueous residue was extracted with ethyl acetate (3×50 ml), and the extracts were dried over sodium sulphate and concentrated. Chromatography on silica gel 60 (<230 mesh ASTM) eluting with ethyl acetate grading to ethyl acetate/ethanol 19:1 gave (3S, 4R)-4-(2-hydroxyethyl)-3-[(1R)-1-p-nitrobenzyloxycarbonyloxyethyl]-azetidin-2-one (9) as a colourless gum (1.08 g); [α]$_D^{20}$+2.6° (c 1 in CHCl$_3$); ν$_{max.}$ (CHCl$_3$) 3 400, 3 300 br, 1 745, 1 605, and 1 525 cm$^{-1}$; δ (CDCl$_3$) 1.48 (3H, d, J 6 Hz, CH$_3$), 1.61 (1 H, br s, OH), 1.8–2.0 (2 H, m, C4—CH$_2$), 3.06 (1 H, ddd, J 8, 2, and 1 Hz, 3-H), 3.6–3.9 (3 H, m, 4-H and CH$_2$—O), 5.13 (1 H, dq, J 8 and 6 Hz, CH—O), 5.25 (2 H, s, benzyl CH$_2$), 6.11 (1 H, br, NH), 7.54 and 8.25 (4 H, 2d, J 9 Hz, nitrobenzyl) (Found: M$^+$-H$_2$O, 320.098 5. C$_{15}$H$_{18}$N$_2$O$_7$-H$_2$O requires M, 320.100 8).

This material is converted to

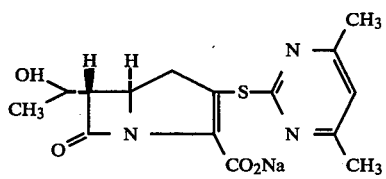

by the methods of European Patent Application Publication No. 0008514.

I claim:

1. A compound of the formula (I)

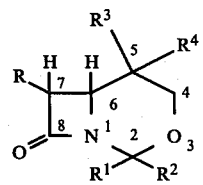

wherein R is acetyl, α-hydroxyethyl or a protected derivative thereof, and R$^1$ and R$^2$ are hydrocarbon groups, or are joined so as to form a carbocyclic or heterocyclic ring, where the carbocyclic or heterocyclic ring contains from 3 to 8 ring atoms and the heterocyclic ring contains two or three heteroatoms selected from oxygen, nitrogen and sulphur any of said R$^1$ and/or R$^2$ groups being unsubstituted or substituted by hydroxy, bromine, chlorine, fluorine, carboxylic acid or salt or ester thereof, azido, tetrazolyl, alkanoyl, alkanoyloxy, aroyloxy, aroyl, aralkanoyloxy, aroxy, amino, protected amino, nitro, C$_{1-6}$ alkoxy, C$_{1-6}$ alkyl, aryl, C$_{1-6}$ alkylthio and arylthio, at least one of R$^1$ and R$^2$ containing a chiral centre; and R$^3$ and R$^4$ are independently hydrogen, a hydrocarbon group, a heterocyclyl group or heterocyclyl (C$_{1-6}$) alkyl wherein the heterocyclic rings contain 1 to 4 heteroatoms selected from oxygen, nitrogen and sulphur atoms, said groups bonded via a carbon atom to the tetrahydro-oxazine ring, or R$^3$ and R$^4$ are joined so as to form together with the carbon atom to which they are attached an C$_{3-7}$ cycloalkyl ring.

2. A compound as claimed in claim 1 which is (6R,7S)-7-acetyl-8-oxo-3-aza-1-azabicyclo[4.2.0]octane-2-spiro-1'-[(3'R)-3'-methylcyclohexane] or (6R,7S)-7-[(1R)-1-hydroxyethyl]-8-oxo-3-oxa-1-azabicyclo[4.2.0]octane-2-spiro-1'-[(3'R)-3'-methylcyclohexane].

3. An enantiomer of a compound of the formula (I) as claimed in claim 1.

* * * * *